United States Patent
Lee et al.

(10) Patent No.: US 11,399,749 B2
(45) Date of Patent: Aug. 2, 2022

(54) OPTICAL SENSOR, METHOD OF MEASURING OPTICAL SIGNAL, AND APPARATUS FOR ESTIMATING BLOOD CONCENTRATION OF ANALYTE

(71) Applicant: SAMSUNG ELECTRONICS CO., LTD., Suwon-si (KR)

(72) Inventors: Joon Hyung Lee, Seongnam-si (KR); Kak Namkoong, Seoul (KR); Jung Yong Nam, Hwaseong-si (KR); Yeol Ho Lee, Anyang-si (KR); Ki Young Chang, Seoul (KR); Won Jong Jung, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 357 days.

(21) Appl. No.: 16/662,771

(22) Filed: Oct. 24, 2019

(65) Prior Publication Data
US 2020/0138341 A1 May 7, 2020

(30) Foreign Application Priority Data
Nov. 6, 2018 (KR) .......................... 10-2018-0135350

(51) Int. Cl.
*A61B 5/1455* (2006.01)
*A61B 5/145* (2006.01)

(52) U.S. Cl.
CPC ........ *A61B 5/1455* (2013.01); *A61B 5/14546* (2013.01)

(58) Field of Classification Search
None
See application file for complete search history.

(56) References Cited

U.S. PATENT DOCUMENTS

| 10,188,328 B2 | 1/2019 | Shimizu et al. |
| 10,485,461 B2 | 11/2019 | Chang et al. |

(Continued)

FOREIGN PATENT DOCUMENTS

| EP | 2 930 495 A1 | 10/2015 |
| EP | 3 275 364 A1 | 1/2018 |

OTHER PUBLICATIONS

Antonio M. Chiarelli et al., "Low-resolution mapping of the effective attenuation coefficient of the human head: a multidistance approach applied to high-density optical recordings", Neurophotonics vol. 4 (2), 021103 (2017), (18 pages total).

(Continued)

*Primary Examiner* — Marjan Fardanesh
(74) *Attorney, Agent, or Firm* — Sughrue Mion, PLLC (57) ABSTRACT

Provided is an optical sensor, including a light source configured to emit light; a photodetector array comprising a plurality of photodetectors positioned at different distances from the light source, each photodetector being configured to detect an optical signal returning from an object irradiated by the light emitted by the light source, and to measure a light intensity of the detected optical signal; and a processor configured to determine a correlation coefficient between variables based on the measured light intensity, and to determine a quality of the optical signal based on the determined correlation coefficient, an optical characteristic of the object being determined by selectively using the optical signal of which the quality is an acceptable level or higher.

22 Claims, 9 Drawing Sheets

(56) References Cited

U.S. PATENT DOCUMENTS

2015/0313516 A1* 11/2015 Shimizu ............ A61B 5/14546
600/322
2016/0058312 A1  3/2016 Han et al.
2016/0299007 A1  10/2016 Kleczewski
2019/0110720 A1  4/2019 Shimizu et al.

OTHER PUBLICATIONS

Yong-Wu RI et al., "Theoretical prediction of the source-detector separation distance suited to the application of the spatially resolved spectroscopy from the near-infrared attenuation data cube of tissues", Department of Chemistry and Department of Physics, Kim II Sung University, arXiv:1409.4246, 2014, pp. 1-9, (9 pages total).

Ri Yong-U et al., "Determination of Oxygen Saturation and Photoplethysmogram from Near Infrared Scattering Images", Faculty of Chemistry, Kim II Sung University, arXiv:1604.06855, 2016 (12 pages total).

Agathe Puszka, "Diffuse optical tomography: a time-resolved approach for reflectance measurements at short source-detector separation", Universite de Grenoble, 2013, pp. 1-228, (245 pages total).

Jesse C. Craig et al., "Effect of adipose tissue thickness, muscle site, and sex on near-infrared spectroscopy derived total- [hemoglobin + myoglobin]", American Physiological Society, 2017, pp. 1571-1578, (9 pages total).

D. M. Hueber et al., "Non-invasive and quantitative near-infrared haemoglobin spectrometry in the piglet brain during hypoxic stress, using a frequency-domain multi distance instrument", Physics in Medicine and Biology, 46 (2001), pp. 41-62 (22 pages total).

Ping Shi et al. "Non-contact Reflection Photoplethysmography Towards Effective Human Physiological Monitoring", Journal of Medical and Biological Engineering, 30 (3): pp. 161-167, (2010) (9 pages total).

Communication dated Mar. 30, 2020, issued by the European Patent Office in counterpart European Application No. 19207209.8.

* cited by examiner

OPTICAL SENSOR, METHOD OF MEASURING OPTICAL SIGNAL, AND APPARATUS FOR ESTIMATING BLOOD CONCENTRATION OF ANALYTE

CROSS-REFERENCE TO RELATED APPLICATION(S)

This application claims priority from Korean Patent Application No. 10-2018-0135350, filed on Nov. 6, 2018, in the Korean Intellectual Property Office, the entire disclosure of which is incorporated herein by reference for all purposes.

BACKGROUND

Field

Example embodiments of the present disclosure relate to non-invasively measuring a blood concentration of an analyte.

Description of the Related Art

Generally, blood triglyceride levels rise for 6 to 7 hours after intake of fat, and begin to fall thereafter. Accordingly, by measuring a variation in triglyceride levels after fat intake, an amount of fat intake, lipolysis ability, and the like may be obtained as important health indicators to be used for healthcare management.

There is a method of invasively measuring triglyceride levels by taking blood samples at intervals of 15 to 20 minutes and analyzing the blood samples. However, while the invasive method of measuring the blood triglyceride levels may provide high reliability in measurement, it may cause pain and inconvenience as well as an increased risk of disease infections due to the use of injection. Recently, research has been conducted on methods of non-invasively estimating a variation in triglyceride levels by measuring optical characteristics without blood sampling.

SUMMARY

One or more example embodiments provide an optical sensor, a method of measuring an optical signal, and an apparatus for estimating a blood concentration of an analyte in a non-invasive manner and with high accuracy.

According to an aspect of an example embodiment, there is provided an optical sensor, including: a light source configured to emit light; a photodetector array comprising a plurality of photodetectors positioned at different distances from the light source, each photodetector being configured to detect an optical signal returning from an object irradiated by the light emitted by the light source, and to measure a light intensity of the detected optical signal; and a processor configured to determine a correlation coefficient between variables based on the measured light intensity, and to determine a quality of the optical signal based on the determined correlation coefficient, an optical characteristic of the object being determined by selectively using the optical signal of which the quality is an acceptable level or higher.

The variables may be obtained from an equation for calculating an effective attenuation coefficient of the object irradiated by the light source.

The correlation coefficient may be a correlation coefficient between $$\ln\left\{\rho^2 \frac{R(\rho)}{S_0}\right\}$$

and $\rho$, wherein $\rho$ denotes a distance between flee light source and a photodetector of the plurality of photodetectors, $R(\rho)$ denotes a light intensity measured by the photodetector positioned away from the light source by the distance $\rho$, and $S_0$ denotes light intensity emitted by the light source.

The correlation coefficient may be a correlation coefficient between $R(\rho)$ and $\rho^{-2}$, wherein $\rho$ denotes a distance between the light source and a photodetector of the plurality of photodetectors, and $R(\rho)$ denotes a light intensity measured by the photodetector positioned away from the light source by the distance $\rho$.

The processor may determine that the quality of the optical signal is the acceptable level or higher based on the determined correlation coefficient exceeding a threshold.

The processor may discard the measured light intensity based on a determination that the quality of the optical signal is less than the acceptable level.

According to an aspect of another example embodiment, there is provided an apparatus for estimating a blood concentration, the apparatus including: a light source configured to emit light; a photodetector array including a plurality of photodetectors positioned at different distances from the light source, each photodetector being configured to detect an optical signal returning from an object irradiated by the light emitted by the light source, and to measure a light intensity of the detected optical signal; and a processor configured to determine a correlation coefficient between variables based on the measured light intensity, to determine a quality of the optical signal based on the determined correlation coefficient, and based on a determination that the quality of the optical signal is an acceptable level or higher, to estimate a blood concentration of an analyte based on the measured light intensity.

The variables may be obtained from an equation for calculating an effective attenuation coefficient of the object irradiated by the light source.

The correlation coefficient may be a correlation coefficient between $$\ln\left\{\rho^2 \frac{R(\rho)}{S_0}\right\}$$

and $\rho$, wherein $\rho$ denotes a distance between the light source and a photodetector of the plurality of photodetectors, $R(\rho)$ denotes a light intensity measured by the photodetector positioned away from the light source by the distance $\rho$, and $S_0$ denotes a light intensity emitted by the light source.

The correlation coefficient may be a correlation coefficient between $R(\rho)$ and $\rho^{-2}$, wherein $\rho$ denotes a distance between e light source and a photodetector of the plurality of photodetectors, and $R(\rho)$ denotes a light intensity measured by the photodetector positioned away from the light source by the distance $\rho$.

Based on the determined correlation coefficient being greater than or equal to a threshold, the processor may determine that the quality of the optical signal is the acceptable level or higher; and based on the determined correlation coefficient being less than the threshold, the processor may determine that the quality of the optical signal is less than the acceptable level.

Based on a determination that the quality of the optical signal is less than the acceptable level, the processor may discard the measured light intensity.

The processor may determine a change in an optical characteristic of the object based on the detected optical signal, and estimate the blood concentration of the analyte by using the determined change in the optical characteristic of the object and a blood concentration estimation model.

The optical characteristics may include at least one of a scattering coefficient or an effective attenuation coefficient.

The analyte may include at least one of glucose, triglyceride, cholesterol, protein, lactate, ethanol, uric acid, or ascorbic acid.

According to an aspect of still another example embodiment, there is provided a method of measuring an optical signal, the method including: emitting, by a light source, light onto an object; detecting an optical signal returning from the object irradiated by the light emitted by the light source, and measuring a light intensity of the detected optical signal; determining a correlation coefficient between variables based on the measured light intensity; and determining a quality of the optical signal based on the determined correlation coefficient, an optical characteristic of the object being determined by selectively using the optical signal of which the quality is an acceptable level or higher.

The variables may be obtained from an equation for calculating an effective attenuation coefficient of the object irradiated by the light source.

The correlation coefficient may be a correlation coefficient between $$\ln\left\{\rho^2 \frac{R(\rho)}{S_0}\right\}$$

and $\rho$, wherein $\rho$ denotes a distance between the light source and a photodetector, $R(\rho)$ denotes a light intensity measured by the photodetector positioned away from the light source by the distance $\rho$, and $S_0$ denotes a light intensity emitted by the light source.

The correlation coefficient may be a correlation coefficient between $R(\rho)$ and $\rho^{-2}$, wherein $\rho$ denotes a distance between the light source and a photodetector, and $R(\rho)$ denotes a light intensity measured by the photodetector positioned away from the light source by the distance $\rho$.

The determining of the quality of the optical signal may include: comparing the determined correlation coefficient with a threshold; based on the determined correlation coefficient exceeding the threshold, determining that the quality of the optical signal is the acceptable level or higher; and based on the determined correlation coefficient being less than or equal to the threshold, determining that the quality of the optical signal is less than the acceptable level.

The method of measuring an optical signal may further include, based on the determined quality of the optical signal being less than the acceptable level, discarding the measured light intensity.

The method of measuring an optical signal may further include, based on the determined quality of the optical signal being less than the acceptable level, repeatedly performing the emitting of the light, the measuring of the light intensity, the determining of the correlation coefficient, and the determining of the quality of the optical signal.

BRIEF DESCRIPTION OF THE DRAWINGS

The above and/or other aspects of the disclosure will become apparent and more readily appreciated from the following description of the example embodiments, taken in conjunction with the accompanying drawings, in which.

DETAILED DESCRIPTION

Hereinafter, example embodiments of the disclosure will be described in detail with reference to the accompanying drawings. It should be noted that wherever possible, the same reference symbols refer to same parts even in different drawings. In the following description, a detailed description of known functions and configurations incorporated herein will be omitted when it may obscure the subject matter of the disclosure. Throughout the drawings and the detailed description, unless otherwise described, the same drawing reference numerals will be understood to refer to the same elements, features, and structures. The relative size and depiction of these elements may be exaggerated for clarity, illustration, and convenience.

Process steps described herein may be performed differently from a specified order, unless the specified order is clearly stated as being necessary in the context of the disclosure. For example, each step may be performed in a specified order, at substantially the same time, or in a reverse order.

Further, the terms used throughout in this specification are defined in consideration of the functions according to example embodiments, and can be varied according to a purpose of a user or manager, or precedent and so on. Therefore, definitions of the terms should be made on the basis of the overall context.

It will be understood that, although the terms first, second, etc. may be used herein to describe various elements, these elements should not be limited by these terms. These terms are only used to distinguish one element from another. Any references to singular may include plural unless expressly stated otherwise. In the specification, it should be understood that the terms, such as 'including' or 'having,' etc., are intended to indicate the existence of the features, numbers, steps, actions, components, parts, or combinations thereof disclosed in the specification, and are not intended to preclude the possibility that one or more other features, numbers, steps, actions, components, parts, or combinations thereof may exist or may be added.

Further, components that will be described in the specification are discriminated merely according to functions mainly performed by the components. That is, two or more components which will be described later can be integrated into a single component. Furthermore, a single component which will be explained later can be separated into two or more components. Moreover, each component which will be described can additionally perform some or all of a function executed by another component in addition to the main function thereof. Some or all of the main function of each component which will be explained can be carried out by another component. Each component may be implemented in hardware or software, or a combination thereof.

In the disclosure, the term "at least one of" includes any and all combinations of one or more of the associated listed items. For example, the term "at least one of A and B" or "at least one of A or B" is only used to describe that three cases may exist: only A exists, both A and B exist, and only B exists. Similarly, "at least one of A, B, and C" or "at least one of A, B, or C" indicates that there may exist seven cases: only A exists, only B exists, only C exists, both A and B exist, both A and C exist, both C and B exist, and all A, B, and C exist.

In the following description, a term 'module,' 'unit,' or 'part' refers to an element that performs at least one function or operation. The 'module' or 'unit' may be realized as hardware, software, or combinations thereof. A plurality of 'modules,' 'units,' or 'parts' may be integrated into at least one module or chip and realized as at least one processor, except for a case where respective 'modules' or 'units' need to be realized as discrete specific hardware.

Figure 1:
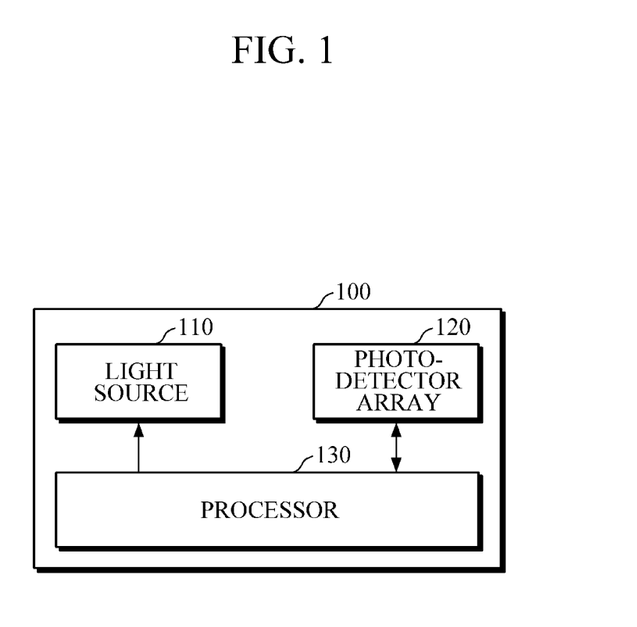
FIG. 1 is a block diagram illustrating an example of an optical sensor according to an example embodiment.

FIG. 1 is a block diagram illustrating an example of an optical sensor 100 according to an example embodiment.

The optical sensor 100 of FIG. 1 is a device for measuring an optical signal with respect to an object, and evaluating quality of the measured optical signal. The optical signal may be a signal generated based on the light emitted by the light source and returning from the object. The optical signal measured by the optical sensor 100 may be used to determine optical characteristics of the object. The optical sensor 100 may be embedded in an electronic device, or may be enclosed in a housing to be provided as a separate device. Examples of the electronic device may include a cellular phone, a smartphone, a tablet PC, a laptop computer, a personal digital assistant (PDA), a portable multimedia player (PMP), a navigation, an MP3 player, a digital camera, a wearable device, and the like; and examples of the wearable device may include a wristwatch-type wearable device, a wristband-type wearable device, a ring-type wearable device, a waist belt-type wearable device, a necklace-type wearable device, an ankle band-type wearable device, a thigh band-type wearable device, a forearm band-type wearable device, and the like. However, the electronic device is not limited to the above examples, and the wearable device is neither limited thereto.

Referring to FIG. 1, the optical sensor 100 includes a light source 110, a photodetector array 120, and a processor 130. Here, the processor 130 may include one or more processors, a memory, or a combination thereof.

The light source 110 may emit light onto an object. For example, the light source 110 may emit light of a specific wavelength, e.g., near infrared (NIR) light, onto an object. However, wavelengths of light to be emitted by the light source 110 may vary depending on a purpose of measurement and/or the types of analytes. Further, the light source 110 is not necessarily a single light-emitting body, and may be formed as an array of a plurality of light-emitting bodies. In the case where the light source 110 is formed as an array of a plurality of light-emitting bodies, the plurality of light-emitting bodies may emit light of different wavelengths, or may emit light of the same wavelength. Further, some of the plurality of light-emitting bodies may emit light of the same wavelength, and others may emit light of different wavelengths. In an example embodiment, the light source 110 may include a light-emitting diode (LED), a laser diode, a fluorescent body, and the like, but these are merely examples, and the disclosure is not limited thereto.

The photodetector array 120 may detect an optical signal at each distance from the light source 110, and may measure a light intensity of the detected optical signal. To this end, the photodetector array 120 may include a plurality of photodetectors positioned at different distances from the light source 110. Each photodetector may detect an optical signal reflected or scattered from an object, and may measure a light intensity of the detected optical signal. In an example embodiment, each photodetector Wray include a photo diode, a photo transistor (PTr), a charge-coupled device (CCD), and the like, but is not limited thereto.

The processor 130 may control the overall operation of the optical sensor 100.

The processor 130 may determine a correlation coefficient between predetermined variables based on the light intensity measured by the photodetector array 120. In an example embodiment, the variables for determining the correlation coefficient may be obtained using an equation for calculating an effective attenuation coefficient of the object irradiated by the light source. The effective attenuation coefficient calculating equation may be expressed by the following Equation 1 or Equation 2.

$$\ln\left\{\rho^2 \frac{R(\rho)}{S_0}\right\} = -\mu_{\mathit{eff}}\rho + \ln\frac{3\mu_a}{2\pi\mu_{\mathit{eff}}} \qquad \text{[Equation 1]}$$

$$R(\rho) = \frac{S_0}{2\pi}\frac{3\mu_a}{\mu_{\mathit{eff}}}\frac{1}{\rho^2}e^{-\mu_{\mathit{eff}}\rho} \qquad \text{[Equation 2]}$$

In Equations 1 and 2, $\rho$ denotes a distance between the light source and the photodetector, $R(\rho)$ denotes a light intensity measured by the photodetector at a position which is away from the light source by the distance $\rho$, $S_0$ denotes a light intensity emitted by the light source to the object, $\mu_{\mathit{eff}}$ denotes an effective attenuation coefficient, and $\rho_a$ denotes an absorption coefficient. Here, $S_0$ may be a value determined experimentally.

In an example embodiment, the processor 130 may determine a correlation coefficient (hereinafter referred to as a first correlation coefficient) between $$\ln\left\{\rho^2 \frac{R(\rho)}{S_0}\right\}$$

and $\rho$ by using $$\ln\left\{\rho^2 \frac{R(\rho)}{S_0}\right\}$$

and $\rho$ of Equation 1 as variables.

In another embodiment, the processor 130 may determine a correlation (hereinafter referred to as a second correlation coefficient) coefficient between R(ρ) and $\rho^{-2}$ by using R(ρ) and $\rho^{-2}$ of Equation 2 as variables.

The processor 130 may determine the quality of the optical signal detected by the photodetector array 120 based on the determined correlation coefficient (the first correlation coefficient and/or the second correlation coefficient). For example, the processor 130 may compare the correlation coefficient (the first correlation coefficient and/or the second correlation coefficient) with a predetermined threshold; and in response to the correlation coefficient exceeding the predetermined threshold, the processor 130 may determine that the quality of the optical signal is an acceptable level or higher (or good quality), and in response to the correlation coefficient being less than or equal to the predetermined threshold, the processor 130 may determine that the quality of the optical signal is less than the acceptable level (or poor quality).

Upon determining that the quality of the optical signal detected by the photodetector array 120 is an acceptable level or higher, the processor 130 may terminate measurement, and may provide the measured light intensity to an apparatus for measuring optical characteristics of an object.

On the other hand, upon determining that the quality of the optical signal detected by the photodetector array 120 is less than the acceptable level, the processor 130 may discard measured values and/or may control the light source 110 and the photodetector array 120 to re-emit light and re-measure a light intensity.

Figure 2:
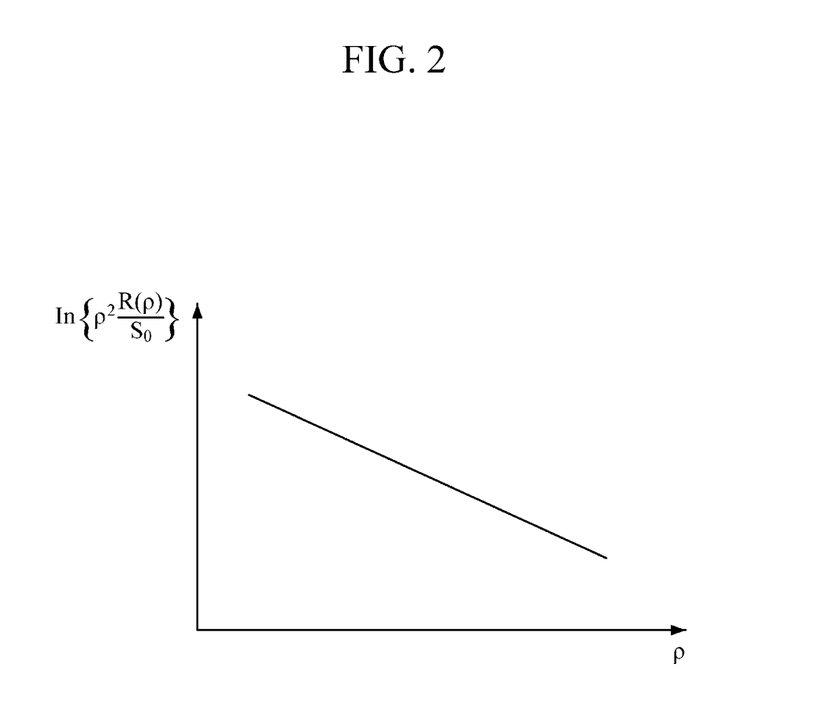
FIG. 2 is a graph illustrating an example of an effective attenuation coefficient calculating equation according to an example embodiment.

FIG. 2 is a graph illustrating an example of an effective attenuation coefficient calculating equation. FIG. 2 may be a graph showing Equation 1.

Referring to FIG. 2, Equation 1 may be shown in a linear graph with a y-axis representing $$\ln\left\{\rho^2 \frac{R(\rho)}{S_0}\right\}$$

and an x-axis representing ρ.

Accordingly, upon plotting $$\ln\left\{\rho^2 \frac{R(\rho)}{S_0}\right\},$$

which is calculated based on the measured light intensity, with respect to ρ, in the case where a result of plotting deviates from linearity, the processor 130 may determine that the quality of the detected optical signal is less than the acceptable level. On the other hand, in the case where a result of the plotting maintains linearity, the processor 130 may determine that the quality of the detected optical signal is an acceptable level or higher. That is, a correlation coefficient between $$\ln\left\{\rho^2 \frac{R(\rho)}{S_0}\right\}$$

and ρ may be used to determine the quality of the detected optical signal.

Figure 3:
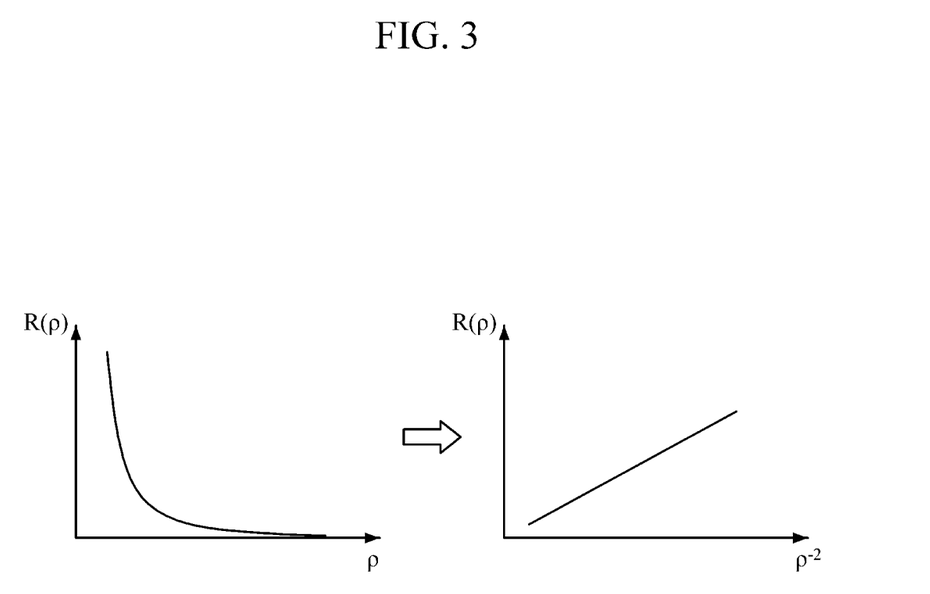
FIG. 3 is a graph illustrating another example of an effective attenuation coefficient calculation equation according to an example embodiment.

FIG. 3 is a graph illustrating another example of an effective attenuation coefficient calculation equation. FIG. 3 may be a graph showing Equation 2.

Referring to FIG. 3, Equation 2 may be shown in a power function graph with a y-axis representing R(ρ) and an x-axis representing ρ, as shown in the left graph; and Equation 2 may be shown in a linear graph with a y-axis representing R(ρ) and an representing $\rho^{-2}$, as shown in the right graph.

Accordingly, upon plotting R(ρ), which is the measured light intensity, with respect to $\rho^{-2}$, in the case where a result of plotting deviates from linearity, the processor 130 may determine that the quality of the detected optical signal is less than the acceptable level. On the other hand, in the case where a result of plotting maintains linearity, the processor 130 may determine that the quality of the detected optical signal is an acceptable level or higher. That is, a correlation coefficient between R(ρ) and $\rho^{-2}$ may be used to determine the quality of the detected optical signal.

Figure 4:
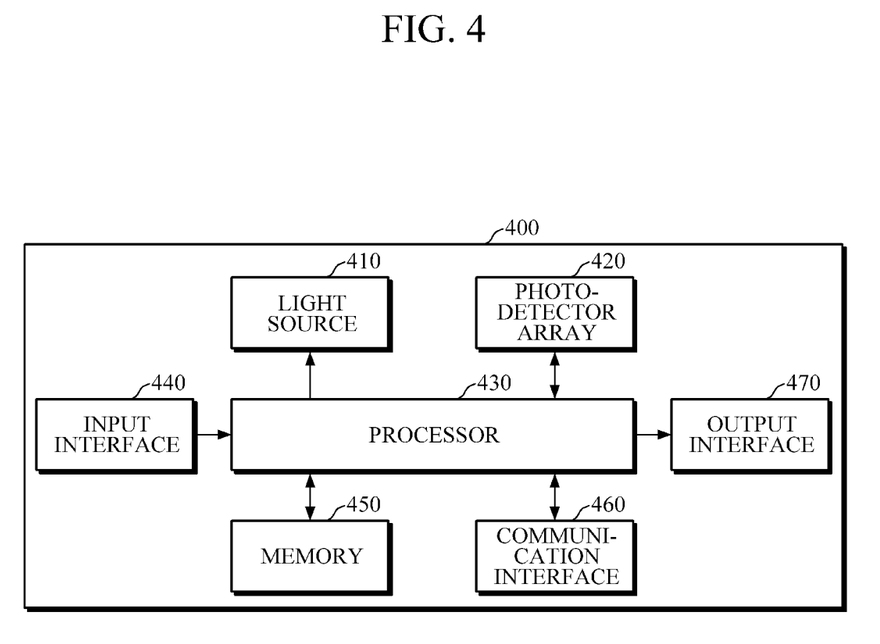
FIG. 4 is a block diagram illustrating another example of an optical sensor according to an example embodiment.

FIG. 4 is a block diagram illustrating another example of an optical sensor. The optical sensor 400 of FIG. 4 is a device for measuring an optical signal upon which optical characteristics of an object is determined, and evaluating quality of the measured optical signal. The optical sensor 400 may be embedded in an electronic device, or may be enclosed in a housing to be provided as a separate device. Examples of the electronic device may include a cellular phone, a smartphone, a tablet PC, a laptop computer, a personal digital assistant (PDA), a portable multimedia player (PMP), a navigation, an MP3 player, a digital camera, a wearable device, and the like; and examples of the wearable device may include a wristwatch-type wearable device, a wristband-type wearable device, a ring-type wearable device, a waist belt-type wearable device, a necklace-type wearable device, an ankle band-type wearable device, a thigh band-type wearable device, a forearm band-type wearable device, and the like. However, the electronic device is not limited to the above examples, and the wearable device is neither limited thereto.

Referring to FIG. 4, the optical sensor 400 includes a light source 410, a photodetector array 420, a processor 430, an input interface 440, a memory 450, a communication interface 460, and an output interface 470. Here, the light source 410 photodetector array 420, and the processor 430 are the same as or substantially similar to the light source 110, the photodetector array 120, and the processor 130 respectively, such that detailed description thereof will be omitted.

The input interface 440 may receive input of various operation signals from a user. In an example embodiment, the input interface 440 may include a keypad, a dome switch, a touch pad (static pressure/capacitance type), a jog wheel, a jog switch, a hardware (H/W) button, and the like. Particularly, the touch pad, which forms a layer structure with a display, may be called a touch screen.

The memory 450 may store programs or commands for operation of the optical sensor 400, and may store data input to and output from the optical sensor 400. Further, memory 450 may store the detected optical signal, the measured light intensity, the determined correlation coefficient, a quality determination result, and the like.

The memory 450 may include at least one storage medium of a flash memory type memory, a hard disk type memory, a multimedia card micro type memory, a card type memory (e.g., an SD memory, an XD memory, etc.), a Random Access Memory (RAM), a Static Random Access Memory (SRAM), a Read Only Memory (ROM), an Electrically Erasable Programmable Read Only Memory (EEPROM), a Programmable Read Only Memory (PROM), a magnetic memory, a magnetic disk, and an optical disk, and the like. Further, the optical sensor 400 may operate an external storage medium, such as web storage and the like, which performs a storage function of the memory 450 on the Internet.

The communication interface 460 may perform communication with an external device. For example, the communication interface 460 may transmit, to the external device, the data input to the optical sensor 400, data stored in and processed by the optical sensor 400, and the like, or may receive, from the external device, various data useful for detecting an optical signal, measuring a light intensity, and determining quality of an optical signal.

In an example embodiment, the external device may be medical equipment using the data input to the optical sensor 400, the data stored in and processed by the optical sensor 400, and the like, and/or the external device may be a printer to print out results, and/or a display to display the results. In addition, the external device may be a digital TV, a desktop computer, a cellular phone, a smartphone, a tablet PC, a laptop computer, a personal digital assistant (PDA), a portable multimedia player (PMP), a navigation, an MP3 player, a digital camera, a wearable device, and the like, but is not limited thereto.

The communication interface 460 may communicate with an external device by using Bluetooth communication, Bluetooth Low Energy (BLE) communication, Near Field Communication (NFC), WLAN communication, Zigbee communication, Infrared Data Association (IrDA) communication, Wi-Fi Direct (WFD) communication, Ultra-Wideband (UWB) communication, Ant+ communication, WIFI communication, Radio Frequency Identification (RFID) communication, 3G communication, 4G communication, 5G communication, and the like. However, this is merely an example and is not intended to be limiting.

The output interface 470 may output the data input to the optical sensor 400, the data stored in and processed by the optical sensor 400, and the like. In an example embodiment, the output interface 470 may output the data input to the optical sensor 400, the data stored in and processed by the optical sensor 400, and the like, by using at least one of an acoustic method, a visual method, and a tactile method. To this end, the output interface 470 may include a display, a speaker, a vibrator, and the like.

Figure 5:
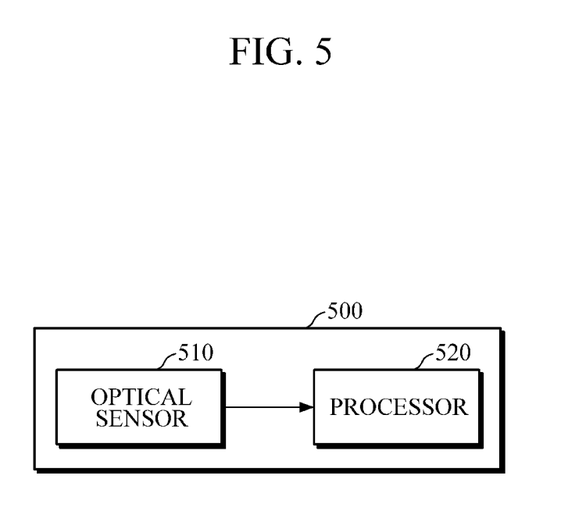
FIG. 5 is a block diagram illustrating an example of an apparatus for estimating a blood concentration according to an example embodiment.

FIG. 5 is a block diagram illustrating an example of an apparatus 500 for estimating a blood concentration. The blood concentration estimating apparatus 500 of FIG. 5 is an apparatus for non-invasively estimating a blood concentration of an analyte or a change in blood concentration of an analyte by using an optical signal, and may be embedded in the aforementioned electronic device or may be enclosed in a housing to be provided as a separate device. Examples of the analyte may include glucose, triglyceride, cholesterol, protein, lactate, ethanol, uric acid, ascorbic acid, and the like.

Referring to FIG. 5, the blood concentration estimating apparatus 500 includes an optical sensor 510 and a processor 520. Here, the optical sensor 510 is the same as the optical sensors 100 and 400 of FIGS. 1 and 4, such that detailed description thereof will be omitted. The processor 520 may be implemented as a separate component from an internal processor of the optical sensor 510, or may be integrally formed with the internal processor of the optical sensor 510.

The processor 520 may control the overall operation of the blood concentration estimating apparatus 500.

The processor 520 may determine a change in optical characteristics based on a light intensity measured by the optical sensor 510. The optical characteristics may include at least one of a scattering coefficient and an effective attenuation coefficient.

In an example embodiment, the processor 520 may determine a scattering coefficient using the following Equation 3, and may determine a change in the scattering coefficient based on the determined scattering coefficient and an initial value of the scattering coefficient.

$$\mu_s' = \frac{1}{3\mu_a}\left\{\frac{1}{\rho_2 - \rho_1}\ln\frac{\rho_1^2 R(\rho_1)}{\rho_2^2 R(\rho_2)}\right\}^2 \quad \text{[Equation 3]}$$

Herein, $\mu_s'$ denotes the scattering coefficient, $\mu_a$ denotes the absorption coefficient, $\rho_1$ denotes a distance between a light source and a first photodetector, $\rho_2$ denotes a distance between a light source and a second photodetector, $R(\rho_1)$ denotes a light intensity measured for each distance by the first photodetector, and $R(\rho_2)$ denotes a light intensity measured for each distance by the second photodetector.

In another embodiment, the processor 520 may determine an effective attenuation coefficient using the aforementioned Equation 1 or Equation 2, and may determine a change in the effective attenuation coefficient based on the determined effect attenuation coefficient and an initial value of the effective attenuation coefficient.

Upon determining a change in optical characteristics, the processor 520 may estimate a change in blood concentration of an analyte by using the determined change in optical characteristics and a blood concentration estimation model. The blood concentration estimation model defines a correlation between the change in optical characteristics and the change in blood concentration of the analyte and may be generated by regression analysis or machine learning. Examples of the regression analysis algorithm may include simple linear regression, multi linear regression, logistic regression, proportional Cox regression, and the like, and examples of the machine learning may include Artificial Neural Network, Decision Tree, Genetic Algorithm, Genetic Programming, K-Nearest Neighbor, Radial Basis Function Network, Random Forest, Support Vector Machine, deep-learning, and the like.

In addition, the processor 520 may estimate a blood concentration based on the estimated change in blood concentration and an initial value of the blood concentration.

Figure 6:
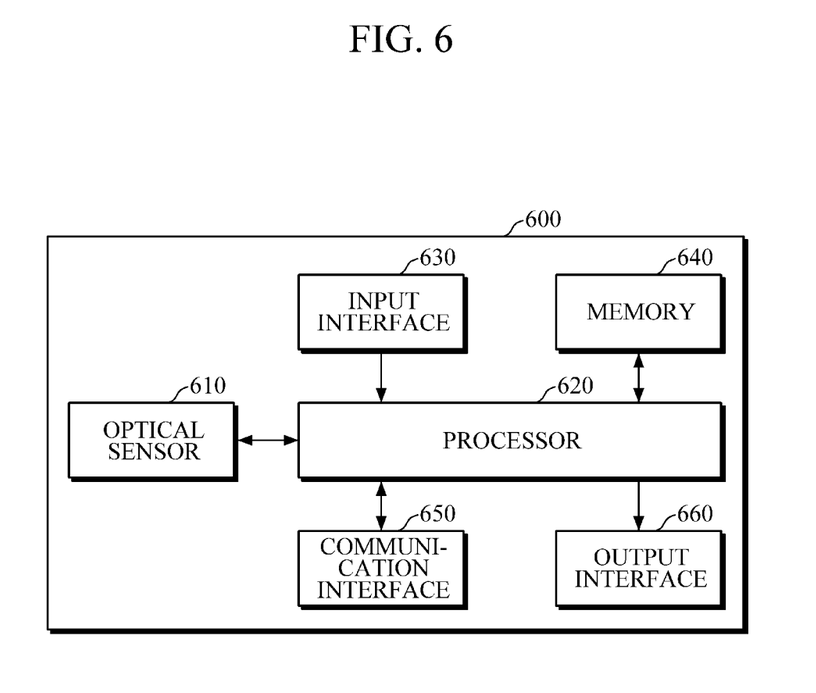
FIG. 6 is a block diagram illustrating another example of an apparatus for estimating a blood concentration according to an example embodiment.

FIG. 6 is a block diagram illustrating another example of an apparatus 600 for estimating a blood concentration. The blood concentration estimating apparatus 600 is an apparatus for non-invasively estimating blood concentration of an analyte or a change in blood concentration of an analyte by using an optical signal, and may be embedded in the aforementioned electronic device or may be enclosed in a housing to be provided as a separate device.

Referring to FIG. 6, the blood concentration estimating apparatus 600 includes an optical sensor 610, a processor 620, an input interface 630, a memory 640, a communication interface 650, and an output interface 660. Here the optical sensor 610 and the processor 620 are the same as or substantially similar to the optical sensor 510 and the processor 520 of FIG. 5 respectively, such that detailed description thereof will be omitted. Further the input interface 630, the memory 640, the communication interface 650, and the output interface 660 of FIG. 6 are the same as or substantially similar to the input interface 440, the memory 450, the communication interface 460, and the output interface 470 of FIG. 4 respectively, such that description thereof will be briefly made.

The input interface 630 may receive input of various operation signals from a user.

The memory 640 may store programs or commands for operation of the blood concentration estimating apparatus 600, and may store data input to and output from the blood concentration estimating apparatus 600. Further, the memory 640 may store the detected optical signal, the measured light intensity, the determined correlation coefficient, a quality determination result, a change in blood concentration of an analyte, a blood concentration of an analyte, and the like.

The communication interface 650 may perform communication with an external device. For example, the communication interface 650 may transmit, to the external device, the data input to the blood concentration estimating apparatus 600, the data stored in and processed by the blood concentration estimating apparatus 600, and the like, or may receive, from the external device, various data useful for detecting an optical signal, measuring a light intensity, determining the quality of an optical signal, determining optical characteristics, estimating a blood concentration of an analyte, and the like.

The output interface 660 may output the data input to the blood concentration estimating apparatus 600, data stored in and processed by the blood concentration estimating apparatus 600, and the like.

Figure 7:
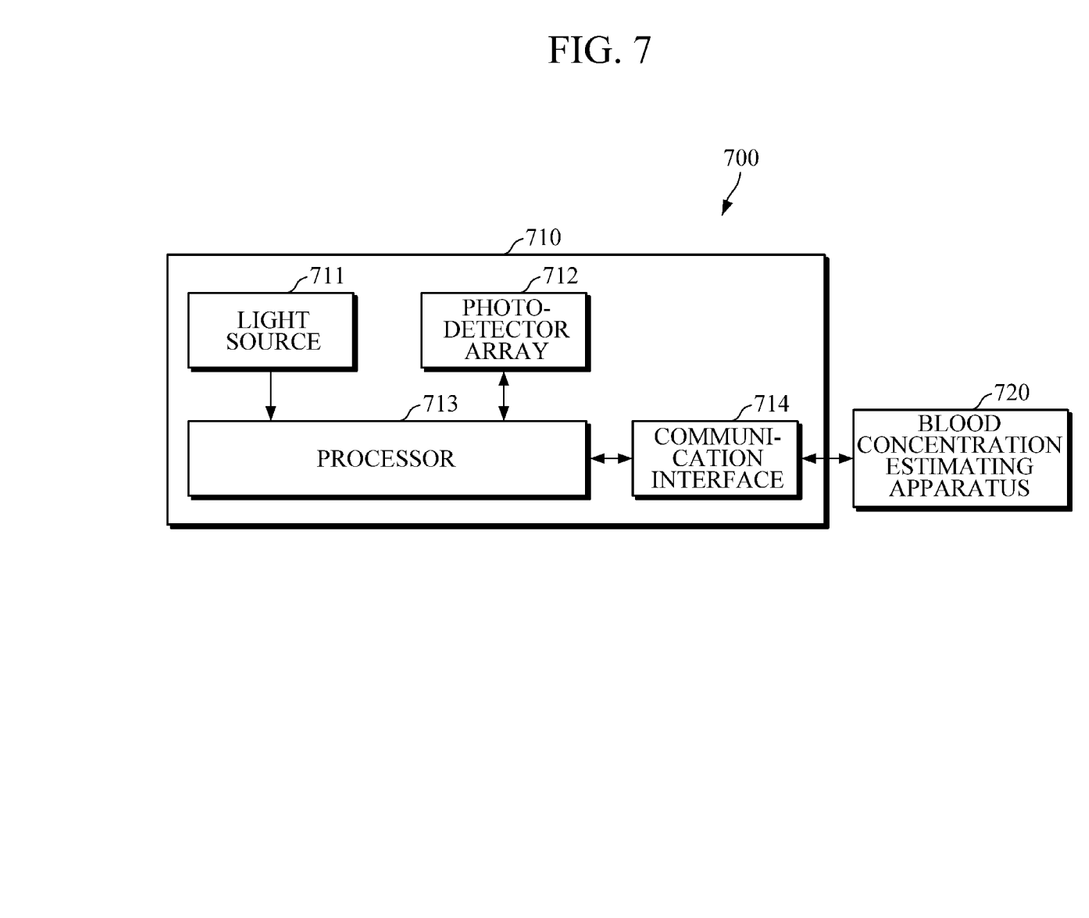
FIG. 7 is a block diagram illustrating an example of a system for estimating a blood concentration according to an example embodiment.

FIG. 7 is a block diagram illustrating an example of a system 700 for estimating a blood concentration. The blood concentration estimating system of FIG. 7 may be an example where an optical sensor and a blood concentration estimating apparatus are provided as separate components.

Referring to FIG. 7, the blood concentration estimating system 700 includes an optical sensor 710 and a blood concentration estimating apparatus 720.

The optical sensor 710 includes a light source 711, a photodetector array 712, a processor 713, and a communication interface 714. The light source 711, the photodetector array 712, and the processor 713 may be the same as or substantially similar to the light source 110, the photodetector array 120, and the processor 130 of FIG. 1 respectively.

That is, the light source 711 may emit light onto an object, and the photodetector array 712 may measure a light intensity by detecting an optical signal returning from the object. The processor 713 may determine the quality of the optical signal based on the measured light intensity; and upon determining that the quality of the optical signal is less than the acceptable level, the processor 713 may discard the measured value and/or may control the light source 711 and the photodetector array 712 to re-emit light and to re-measure a light intensity.

The processor 713 may transmit an optical signal of an acceptable level or higher quality and a light intensity to the blood concentration estimating apparatus 720 through the communication interface 714 by using various communication techniques. For example, the communication techniques may include Bluetooth communication, Bluetooth Low Energy (BLE) communication, Near Field Communication (NFC), WLAN communication, Zigbee communication, Infrared Data Association (IrDA) communication, Wi-Fi Direct (WFD) communication, Ultra-Wideband (UWB) communication, Ant+ communication, WIFI communication, Radio Frequency Identification (RFID) communication, 3G communication, 4G communication, 5G communication, and the like.

The blood concentration estimating apparatus 720 may perform the function of the processor 520 of FIG. 5. That is, the blood concentration estimating apparatus 720 may determine optical characteristics of an object by receiving the optical signal and the light intensity from the optical sensor 710, and may estimate a change in blood concentration of an analyte and/or a blood concentration of the analyte based on the determined optical characteristics.

Figure 8:
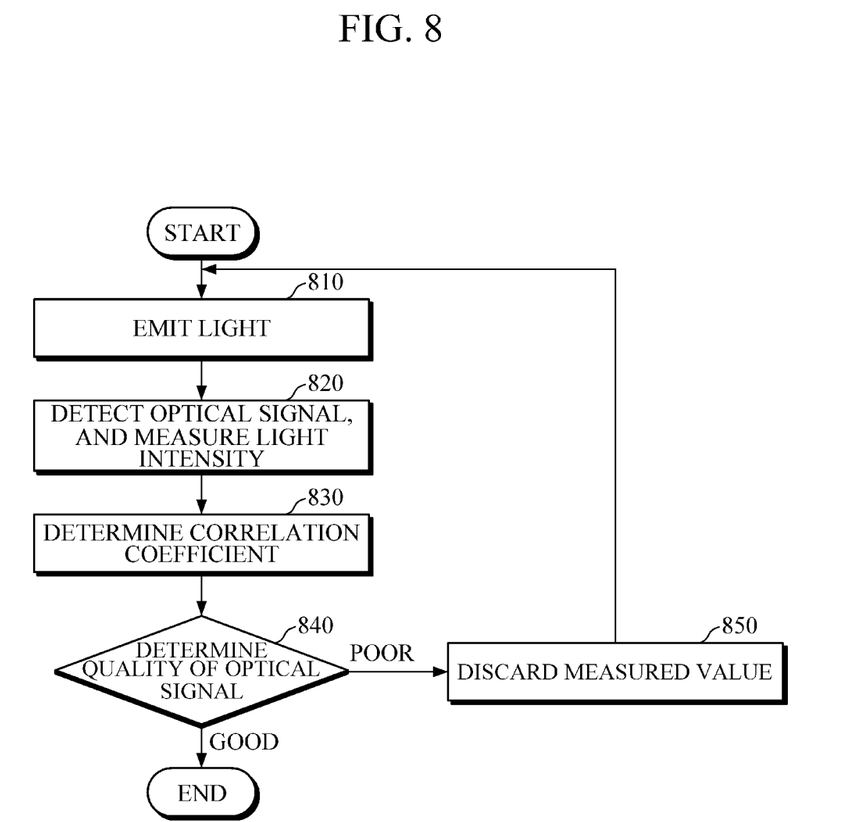
FIG. 8 is a flowchart illustrating an example of a method of measuring an optical signal according to an example embodiment.

FIG. 8 is a flowchart illustrating an example of a method of measuring an optical signal. The optical signal measuring method of FIG. 8 may be performed by the optical sensors 100 and 400 of FIGS. 1 and 4.

Referring to FIG. 8, the optical sensor may emit light onto an object in 810. For example, the optical sensor may emit light of a predetermined wavelength, e.g., near infrared (NIR) light, onto an object. However, wavelengths of light to be emitted by a light source may vary depending on a purpose of measurement and/or the types of analytes.

The optical sensor may detect an optical signal reflected or scattered from the object, and may measure a light intensity of the detected optical signal in 820.

The optical sensor may determine a correlation coefficient between predetermined variables based on the measured light intensity in 830. In an example embodiment, the variables for determining the correlation coefficient may be obtained from an effective attenuation coefficient calculating equation. The effective attenuation coefficient calculating equation may be expressed by Equation 1 or Equation 2.

In an example embodiment, the optical sensor may determine a correlation coefficient between $$\ln\left\{\rho^2 \frac{R(\rho)}{S_0}\right\}$$

and $\rho$ by using $$\ln\left\{\rho^2 \frac{R(\rho)}{S_0}\right\}$$

and $\rho$ of Equation 1 as variables.

In another embodiment, the optical sensor may determine a correlation coefficient between $R(\rho)$ and $\rho^{-2}$ by using $R(\rho)$ and $\rho^{-2}$ of Equation 2 as variables.

The optical sensor may determine the quality of an optical signal based on the determined correlation coefficient in 840. For example, the optical sensor may compare the correlation coefficient with a predetermined threshold Th; and in response to the correlation coefficient exceeding the predetermined threshold Th, the optical sensor may determine that the quality of an optical signal is an acceptable level or higher, and in response to the correlation coefficient being less than or equal to the predetermined threshold Th, the optical sensor may determine that the quality of an optical signal is less than the acceptable level.

Upon determining that the quality of the optical signal is less than the acceptable level, the optical sensor may discard the measured value in 850, and may return to the operation 810 to re-emit light onto an object, re-detect an optical signal, and re-measure a light intensity.

Further, upon determining that the quality of the optical signal is an acceptable level or higher, the optical sensor may terminate measurement.

The discarding of the measured value in 850 of FIG. 8 is not an essential process, and may be omitted if necessary.

Figure 9:
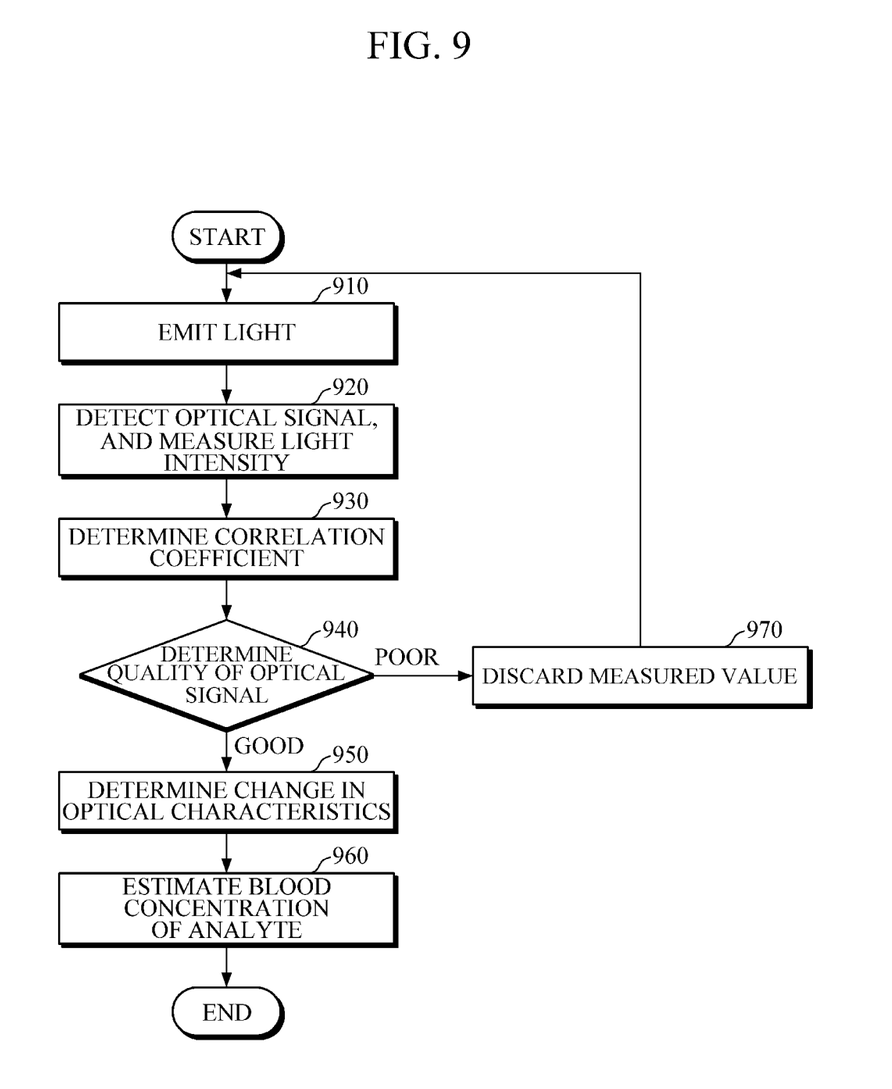
FIG. 9 is a flowchart illustrating an example of a method of estimating a blood concentration of an analyte according to an example embodiment.

FIG. 9 is a flowchart illustrating an example of a method of estimating a blood concentration of an analyte. The blood concentration method of FIG. 9 may be performed by the blood concentration estimating apparatuses 500 and 600 of FIGS. 5 and 6.

Referring to FIG. 9, the blood concentration estimating apparatus may emit light onto an object in 910. For example, the blood concentration estimating apparatus may emit light of a predetermined wavelength (e.g., near infrared (NIR) light) onto an object.

The blood concentration estimating apparatus may detect an optical signal reflected or scattered from the object, and may measure a light intensity of the detected optical signal in 920.

The blood concentration estimating apparatus may determine a correlation coefficient between predetermined variables based on the measured light intensity in 930. In an example embodiment, the variables for determining the correlation coefficient may be obtained from an equation for calculating an effective attenuation coefficient of the object irradiated by the light source. The effective attenuation coefficient calculating equation may be expressed by Equation 1 or Equation 2.

For example, the blood concentration estimating apparatus may determine a correlation coefficient between $$\ln\left\{\rho^2 \frac{R(\rho)}{S_0}\right\}$$

and $\rho$ by using $$\ln\left\{\rho^2 \frac{R(\rho)}{S_0}\right\}$$

and $\rho$ of Equation 1 as variables; or may determine a correlation coefficient between $R(\rho)$ and $\rho^{-2}$ by using $R(\rho)$ and $\rho^{-2}$ of Equation 2 as variables.

The blood concentration estimating apparatus may determine the quality of an optical signal based on the determined correlation coefficient in 940. For example, the blood concentration estimating apparatus may compare the correlation coefficient with a predetermined threshold Th; and in response to the correlation coefficient exceeding the predetermined threshold Th, the blood concentration estimating apparatus may determine that the quality of an optical signal is an acceptable level or higher, and in response to the correlation coefficient being less than or equal to the predetermined threshold Th, the blood concentration estimating apparatus may determine that the quality of an optical signal is less than the acceptable level.

Upon determining that the quality of the optical signal is an acceptable level or higher, the blood concentration estimating apparatus may determine a change in optical characteristics based on the measured light intensity in 950. The optical characteristics may include at least one of a scattering coefficient and an effective attenuation coefficient.

In an example embodiment, the blood concentration estimating apparatus may determine an effective attenuation coefficient by using the aforementioned Equation 1 or Equation 2, and may determine a change in the effective attenuation coefficient based on the determined effective attenuation coefficient and an initial value of the effective attenuation coefficient.

In another embodiment, the blood concentration estimating apparatus may determine a scattering coefficient by using the aforementioned Equation 3, and may determine a change in the scattering coefficient based on the determined scattering coefficient and an initial value of the scattering coefficient.

Upon determining the change in optical characteristics, the blood concentration estimating apparatus may estimate a change in blood concentration of an analyte by using the determined change in optical characteristics and a blood concentration estimation model, and may estimate a blood concentration of the analyte based on the estimated change in blood concentration and an initial value of the blood concentration in 960. The blood concentration estimation model defines a correlation between the change in optical characteristics and the change in blood concentration of the analyte, and may be generated by regression analysis or machine learning. Examples of the regression analysis algorithm may include, but not limited to, simple linear regression, multi linear regression, logistic regression, proportional Cox regression, and the like, and examples of the machine learning may include, but not limited to, Artificial Neural Network, Decision Tree, Genetic Algorithm, Genetic Programming, K-Nearest Neighbor, Radial Basis Function Network, Random Forest, Support Vector Machine, deep-learning, and the like.

Upon determining that the quality of the optical signal is less than the acceptable level, the blood concentration estimating apparatus may discard the measured value in 970, and may return to the operation 910 to re-emit light onto an object, re-detect an optical signal returning from the object, and re-measure a light intensity.

The disclosure can be realized as a computer-readable code written on a computer-readable recording medium. The computer-readable recording medium may be any type of recording device in which data is stored in a computer-readable manner. Examples of the computer-readable recording medium include a ROM, a RAM, a CD-ROM, a magnetic tape, a floppy disc, an optical data storage, and a carrier wave (e.g., data transmission through the Internet). The computer-readable recording medium can be distributed over a plurality of computer systems connected to a network so that a computer-readable code is written thereto and executed therefrom in a decentralized manner. Functional programs, codes, and code segments needed for realizing the disclosure can be easily deduced by one of ordinary skill in the art.

At least one of the components, elements, modules or units described herein may be embodied as various numbers of hardware, software and/or firmware structures that execute respective functions described above, according to an example embodiment. For example, at least one of these components, elements or units may use a direct circuit structure, such as a memory, a processor, a logic circuit, a look-up table, etc. that may execute the respective functions through controls of one or more microprocessors or other control apparatuses. Also, at least one of these components, elements or units may be specifically embodied by a module, a program, or a part of code, which contains one or more executable instructions for performing specified logic functions, and executed by one or more microprocessors or other control apparatuses. Also, at least one of these components, elements or units may further include or implemented by a processor such as a central processing unit (CPU) that performs the respective functions, a microprocessor, or the like. Two or more of these components, elements or units may be combined into one single component, element or unit which performs all operations or functions of the combined two or more components, elements of units. Also, at least part of functions of at least one of these components, elements or units may be performed by another of these components, element or units. Further, although a bus is not illustrated in the block diagrams, communication between the components, elements or units may be performed through the bus. Functional aspects of the above example embodiments may be implemented in algorithms that execute on one or more processors. Furthermore, the components, elements or units represented by a block or processing steps may employ any number of related art techniques for electronics configuration, signal processing and/or control, data processing and the like.

While a few example embodiments have been described above, the scope of the disclosure is not limited thereto and various modifications and improvements made by those of ordinary skill in the art to concepts defined in the following claims should be understood to fall within the scope of the disclosure.

What is claimed is:

1. An optical sensor comprising:
   a light source configured to emit light;
   a photodetector array comprising a plurality of photodetectors positioned at different distances from the light source, each photodetector being configured to detect an optical signal returning from an object irradiated by the light emitted by the light source, and to measure a light intensity of the detected optical signal; and
   a processor configured to determine a correlation coefficient between a first variable based on a distance between the light source and a photodetector of the plurality of photodetectors and a second variable based on a light intensity measured by the photodetector positioned away from the light source by the distance, the correlation coefficient being determined by plotting the second variable with respect to the first variable using a plurality of optical signals detected by the plurality of photodetectors,
   wherein the processor is further configured to compare the correlation coefficient between the first variable and the second variable with a threshold and determine a quality of the optical signal based on a result of comparison.

2. The optical sensor of claim 1, wherein the first variable and the second variable are obtained from an equation for calculating an effective attenuation coefficient of the object irradiated by the light source.

3. The optical sensor of claim 1, wherein the first variable is $\rho$, and the second variable is $$\ln\left\{\rho^2 \frac{R(\rho)}{S_0}\right\}$$

$$\ln\left\{\rho^2 \frac{R(\rho)}{S_0}\right\}$$

$\rho$,
   wherein $\rho$ denotes the distance between the light source and the photodetector of the plurality of photodetectors, $R(\rho)$ denotes the light intensity measured by the photodetector positioned away from the light source by the distance $\rho$, and $S_0$ denotes a light intensity emitted by the light source.

4. The optical sensor of claim 1, wherein the first variable is $\rho^{-2}$, and the second variable is $R(\rho)$ correlation coefficient is a correlation coefficient between $R(\rho)\rho^{-2}$,
   wherein $\rho$ denotes the distance between the light source and the photodetector of the plurality of photodetectors, and $R(\rho)$ denotes the light intensity measured by the photodetector positioned away from the light source by the distance $\rho$.

5. The optical sensor of claim 1, wherein the processor is further configured to determine that the quality of the optical signal is an acceptable level or higher based on the determined correlation coefficient exceeding the threshold.

6. The optical sensor of claim 1, wherein the processor is further configured to discard the measured light intensity based on a determination that the determined correlation coefficient is less than the threshold.

7. An apparatus for estimating a blood concentration, the apparatus comprising:
   a light source configured to emit light;
   a photodetector array comprising a plurality of photodetectors positioned at different distances from the light source, each photodetector being configured to detect an optical signal returning from an object irradiated by the light emitted by the light source, and to measure a light intensity of the detected optical signal; and
   a processor configured to determine a correlation coefficient between a first variable based on a distance between the light source and a photodetector of the plurality of photodetectors and a second variable based on a light intensity measured by the photodetector positioned away from the light source by the distance, the correlation coefficient being determined by plotting the second variable with respect to the first variable using a plurality of optical signals detected by the plurality of photodetectors,
   wherein the processor is further configured compare the correlation coefficient between the first variable and the second variable with a threshold, determine a quality of the optical signal based on a result of comparison, and based on a determination that the quality of the optical signal is an acceptable level or higher, to estimate a blood concentration of an analyte based on the measured light intensity.

8. The apparatus of claim 7, wherein the first variable and the second variable are obtained from an equation for calculating an effective attenuation coefficient of the object irradiated by the light source.

9. The apparatus of claim 7, wherein the first variable is $\rho$, and the second variable is $$\ln\left\{\rho^2 \frac{R(\rho)}{S_0}\right\}$$

$$\ln\left\{\rho^2 \frac{R(\rho)}{S_0}\right\}$$

$\rho$,
   wherein $\rho$ denotes the distance between the light source and the photodetector of the plurality of photodetectors, $R(\rho)$ denotes the light intensity measured by the photodetector positioned away from the light source by the distance $\rho$, and $S_0$ denotes a light intensity emitted by the light source.

10. The apparatus of claim 7, wherein the first variable is $\rho^{-2}$, and the second variable is $R(\rho)R(\rho) \rho^{-2}$, wherein $\rho$ denotes the distance between the light source and the photodetector of the plurality of photodetectors, and $R(\rho)$ denotes the light intensity measured by the photodetector positioned away from the light source by the distance $\rho$.

11. The apparatus of claim 7, wherein:
based on the determined correlation coefficient being greater than or equal to the threshold, the processor is further configured to determine that the quality of the optical signal is the acceptable level or higher, and
based on the determined correlation coefficient being less than the threshold, the processor is further configured to determine that the quality of the optical signal is less than the acceptable level.

12. The apparatus of claim 7, wherein based on a determination that the determined correlation coefficient is less than the threshold, the processor is further configured to discard the measured light intensity.

13. The apparatus of claim 7, wherein the processor is further configured to determine a change in an optical characteristic of the object based on the detected optical signal, and estimate the blood concentration of the analyte by using the determined change in the optical characteristic of the object and a blood concentration estimation model.

14. The apparatus of claim 13, wherein the optical characteristic comprises at least one of a scattering coefficient or an effective attenuation coefficient.

15. The apparatus of claim 7, wherein the analyte comprises at least one of glucose, triglyceride, cholesterol, protein, lactate, ethanol, uric acid, or ascorbic acid.

16. A method of measuring an optical signal, the method comprising:
emitting, by a light source, light onto an object;
detecting, by a plurality of photodetectors, an optical signal returning from the object irradiated by the light emitted by the light source, and measuring a light intensity of the detected optical signal; and
determining a correlation coefficient between a first variable based on a distance between the light source and a photodetector of the plurality of photodetectors and a second variable based on a light intensity measured by the photodetector positioned away from the light source by the distance, the correlation coefficient being determined by plotting the second variable with respect to the first variable using a plurality of optical signals detected by the plurality of photodetectors,
wherein the method further comprises comparing the correlation coefficient between the first variable and the second variable with a threshold and determining a quality of the optical signal based on a result of comparison.

17. The method of claim 16, wherein the first variable and the second variable are obtained from an equation for calculating an effective attenuation coefficient of the object irradiated by the light source.

18. The method of claim 16, wherein the first variable is $\rho$, and the second variable is $$\ln\left\{\rho^2 \frac{R(\rho)}{S_0}\right\}$$

$$\ln\left\{\rho^2 \frac{R(\rho)}{S_0}\right\}$$

$\rho$, wherein $\rho$ denotes the distance between the tight source and the photodetector, $R(\rho)$ denotes the light intensity measured by the photodetector positioned away from the light source by the distance $\rho$, and $S_0$ denotes a light intensity emitted by the light source.

19. The method of claim 16, wherein the first variable is $\rho^{-2}$, and the second variable is $R(\rho) R(\rho) \rho^{-2}$,
wherein $\rho$ denotes the distance between the light source and a photodetector, and $R(\rho)$ denotes the light intensity measured by the photodetector positioned away from the light source by the distance $\rho$.

20. The method of claim 16, wherein the determining of the quality of the optical signal comprises:
based on the determined correlation coefficient exceeding the threshold, determining that the quality of the optical signal is an acceptable level or higher; and
based on the determined correlation coefficient being less than or equal to the threshold, determining that the quality of the optical signal is less than the acceptable level.

21. The method of claim 16, further comprising, based on the correlation coefficient being less than the threshold, discarding the measured light intensity.

22. The method of claim 16, further comprising, based on the determined quality of the optical signal being less than an acceptable level, repeatedly performing the emitting of the light, the measuring of the light intensity, the determining of the correlation coefficient, and the determining of the quality of the optical signal.

* * * * *